(12) United States Patent
Cui et al.

(10) Patent No.: US 9,010,935 B2
(45) Date of Patent: Apr. 21, 2015

(54) SYSTEMS AND METHODS FOR NONINVASIVE ANALYSIS OF RETINAL HEALTH AND FUNCTION

(71) Applicant: California Institute of Technology, Pasadena, CA (US)

(72) Inventors: Xiquan Cui, Pasadena, CA (US); Scott E. Fraser, Glendale, CA (US)

(73) Assignee: California Institute of Technology, Pasadena, CA (US)

(*) Notice: Subject to any disclaimer, the term of this patent is extended or adjusted under 35 U.S.C. 154(b) by 255 days.

(21) Appl. No.: 13/683,992

(22) Filed: Nov. 21, 2012

(65) Prior Publication Data

US 2013/0128227 A1 May 23, 2013

Related U.S. Application Data

(60) Provisional application No. 61/562,970, filed on Nov. 22, 2011.

(51) Int. Cl.
- *A61B 3/10* (2006.01)
- *A61B 3/00* (2006.01)
- *A61B 3/12* (2006.01)

(52) U.S. Cl.
CPC .... *A61B 3/12* (2013.01); *A61B 3/10* (2013.01)

(58) Field of Classification Search
USPC ................................. 351/206, 211, 221, 246
See application file for complete search history.

(56) References Cited

U.S. PATENT DOCUMENTS

| | | | |
|---|---|---|---|
| 2009/0118601 A1 | 5/2009 | Rabolt et al. | |
| 2009/0153797 A1 | 6/2009 | Allon et al. | |
| 2009/0306521 A1 | 12/2009 | Ermakov et al. | |
| 2011/0116041 A1 | 5/2011 | Hartung et al. | |

FOREIGN PATENT DOCUMENTS

WO WO 2013078412 5/2013

OTHER PUBLICATIONS

ISR for PCT/US2012/066393.
Written Opinion for PCT/US2012/066393.

*Primary Examiner* — Jack Dinh
(74) *Attorney, Agent, or Firm* — Hema Vakharia-Rao; Nixon Peabody LLP

(57) ABSTRACT

A method for noninvasive analysis of a retina includes exposing the retina to one or more first sets of at least three illumination light signals. The at least three illumination light signals each have a different wavelength. The method also includes optically collecting a reflected light signal for each of the at least three illumination light signals of the one or more first sets. Each of the reflected light signals is a portion of the respective illumination light signal reflected by the retina. The method further includes detecting the reflected light signals of the one or more first sets as a function of intensity. The method still further includes determining a first opsin density using the detected intensity of each of the reflected light signals of the one or more first sets.

26 Claims, 5 Drawing Sheets

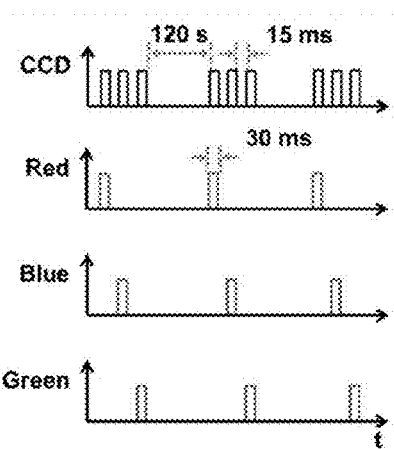
FIG. 3
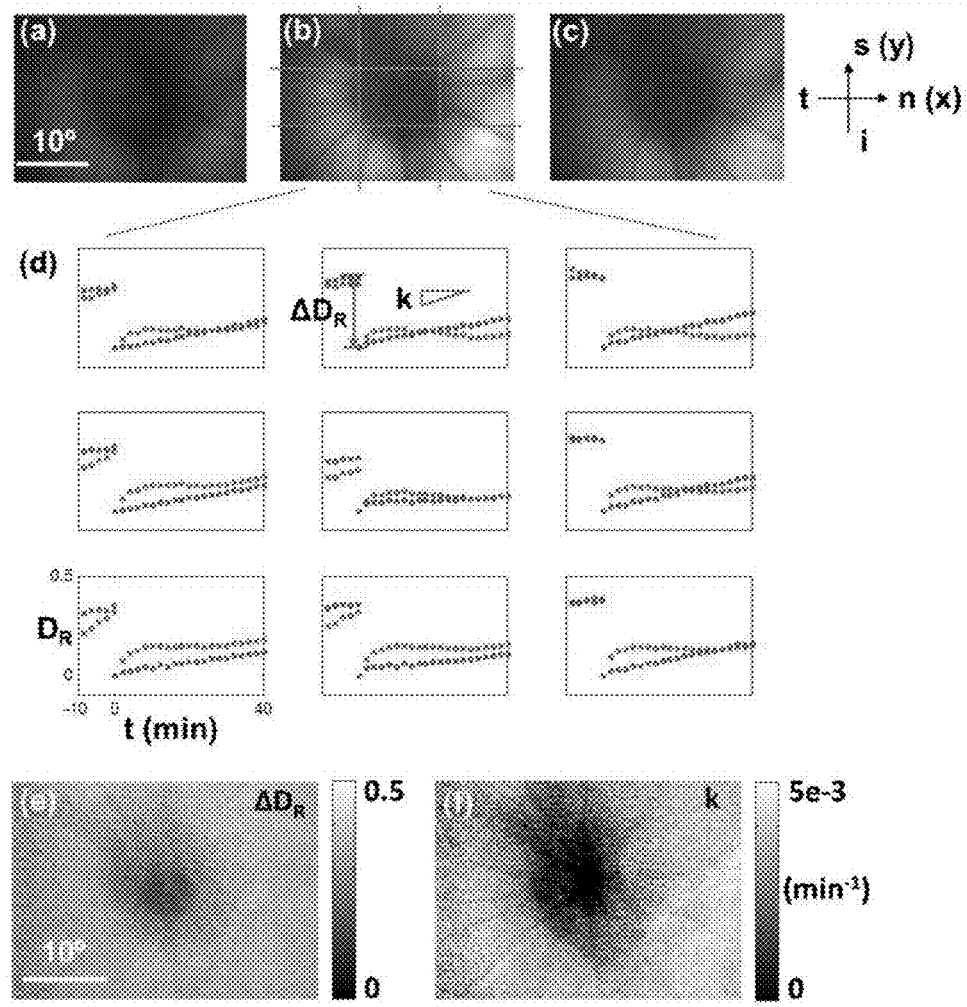
FIGS. 4a-f

SYSTEMS AND METHODS FOR NONINVASIVE ANALYSIS OF RETINAL HEALTH AND FUNCTION

CROSS-REFERENCE TO RELATED APPLICATION

This application claims priority of U.S. Ser. No. 61/562,970 filed Nov. 22, 2011, the contents of which are herein incorporated by reference.

FIELD OF THE INVENTION

The present invention relates generally to systems and methods for evaluating an eye and, more particularly, to systems and methods for an evaluation of health and functionality of a retina.

BACKGROUND OF THE INVENTION

The sense of sight involves receiving and focusing electromagnetic energy in the visible spectrum onto a retina of an eye, which converts the electromagnetic energy into signals that can be processed by the nervous system. The process by which photons of light are converted includes a cyclic decomposition and reconstitution of various proteins and enzymes within the photoreceptor cells of the retina. The photoreceptor cells include an opsin (e.g., rhodopsin in rod cells or photopsin in cone cells) bound to 11-cis retinal, a photosensitive derivative of vitamin A. Energy from incident light converts the 11-cis retinal to a different configuration, all-trans retinal, which changes the conformation of the opsin, leading to signal transduction. As a result, the opsin progressively breaks up into a number of intermediate compounds (e.g., metarhodopsin II and metarhodopsin III). For the photoreceptor cells to be able to respond to new light, the opsin needs to be reconstituted. The retinal pigment epithelium cells play a substantial role in the reconstitution by receiving the all-trans retinal from the photoreceptor cells and returning 11-cis retinal, which then recombines with an opsin to form new, functional visual pigment molecules. The retina is constantly exposed to light, requiring constant refreshing of the eyes to maintain functionality. Thus, the photoreceptor cells ability to be "recharged" by the retinal pigment epithelium cells is fundamental and indispensible to the sense of sight.

Unfortunately, a number of retinal diseases and conditions can cause failure or loss of photoreceptor cell or retinal pigment epithelium functionality, leading to significant loss of visual ability or even blindness. For example, age-related macular degeneration, geographic atrophy, retinitis pigmentosa, stargardt disease, macular telangiectasia, and other diseases have been known or are believed to cause failure or loss of photoreceptor or retinal pigment epithelium functionality are all retinal diseases that affect the functionality of the photoreceptor cell or retinal pigment epithelium cells. For some diseases, there is no device that can provide adequate assessment of the health and functionality of the photoreceptors and retinal pigment epithelium cells. This has severely hindered the advancement of research, classification, diagnosis, treatment, and patient management in connection with retinal diseases and conditions. For other diseases, present assessment techniques may be minimally adequate and could greatly benefit from new techniques providing more fine-grained analysis of disease pathogenesis, evaluation of treatment efficacies, and quantitative management of disease patients.

In particular, for example, age-related macular degeneration is a major public health problem. It destroys a patient's sharp and central vision in and around the macular region, significantly impacting the patient's ability to perform everyday activities (e.g., reading, driving, facial recognition, etc.) and degrading the patient's quality of life. Age-related macular degeneration currently affects over eight million people in the United States and is the leading cause of vision loss for people over 60 years old. As the aging population grows, the occurrence of age-related macular degeneration is expected to increase by over 50% by 2020. Not only will patients' suffer, a significant burden may also be imposed on society, for example, due to patients' loss of independence, rising health care costs associated with age-related macular degeneration medical expenses, and injuries (e.g., falling due to poor vision).

Currently, age-related macular degeneration is classified into two forms—a dry form (nonexudative) and a wet form (exudative). In the wet form of age-related macular degeneration, a patient's newly grown and fragile blood vessels leak blood into the retina, prohibiting clear viewing and/or damaging the retina, and potentially causing the retina to become detached from the choroid. In the dry form, drusen (i.e., yellow cellular deposits) accumulate between the retina and the choroid, causing atrophy of the retinal pigment epithelial cells and vision loss through the loss of photoceptor cells in the central part of the eye. Depending on the stage of the disease, the patient's vision may not change, become blurred, and/or become dark in areas. While treatments have been developed for the wet form of age-related macular degeneration (e.g., laser surgery, photodynamic therapy, and anti-VEGF injunctions), there is presently no FDA-approved treatment for the dry form of age-related macular degeneration.

At present, little is known about the causes of diseases such as age-related macular degeneration. The symptoms associated with age-related macular degeneration vary greatly and a number of different genes have been identified as potentially related to age-related macular degeneration. One hypothesis is that age-related macular degeneration is actually a group of retinal diseases. Currently, the presence of drusen is considered the clinical hallmark of dry form age-related macular degeneration. However, such diagnosis and classification is not adequate because the presence of drusen is ubiquitous for people over 50 years old and is considered to be associated with the natural aging process. Accordingly, only considering the presence and amount of drusen is inadequate for researching, classifying, diagnosing or treating the disease.

Indeed, there is no adequate system or method for researching, classifying, diagnosing or treating the age-related macular degeneration. The conventional fundus photography device is most widely used to provide a clear and color image of the retina and exam legions. However, because drusen is a part of the natural aging process, fundus photography images of drusen alone is not sufficient for complicated diseases such as age-related macular degeneration. Fluorescent angiography is a standard technique for detecting excess growth and/or leakage of blood vessels on the retina. While this technique is useful in the context of wet form age-related macular degeneration, it has little applicability to other diseases such as, for example, dry form age-related macular degeneration.

Optical coherence tomography is an emerging noninvasive retina imaging technology that can provide a three-dimensional view of the retinal structures using reflected light. It has been used to monitor the progress and to treat the wet form of age-related macular degeneration. However, optical coherence tomography can be sensitive to the change of the retinal structures and is not specific to the function of the retina. Although a functional optical coherence tomography technique has been developed, its sensitivity is low and its specificity to the retina health is unclear.

Another technique that has been attempted utilizes autofluorescence. In particular, autofluorescence of lipofuscin accumulation in retinal pigment epithelium cells was used to mark the stress levels of the retinal pigment epithelium cells. Although this technique may be informative, recent histology studies show that the autofluorescence of retinal pigment epithelium cells is not necessarily correlated with the loss of photoreceptor cells. It was found that the low level of autofluorescence may represent either healthy or completely dead retinal pigment epithelium cells, and a retina with a high level of autofluorescence may still have functioning photoreceptor and retinal pigment epithelium cells.

SUMMARY OF THE INVENTION

According to one aspect of the present invention, a method for noninvasive analysis of a retina includes exposing the retina to one or more first sets of at least three illumination light signals generated by one or more light sources. The at least three illumination light signals each have a different wavelength. The method also includes optically collecting a reflected light signal for each of the at least three illumination light signals of the one or more first sets. Each of the reflected light signals is a portion of the respective illumination light signal reflected by the retina. The method further includes detecting, via a light detector, the reflected light signals of the one or more first sets as a function of intensity. The method still further includes determining, via one or more processors, a first opsin density using the detected intensity of each of the reflected light signals of the one or more first sets.

According to another aspect of the present invention, a system for noninvasive analysis of a retina includes one or more light sources configured to generate at least three illumination light signals. Each of the at least three illumination light signals have a different wavelength. The system also includes one or more optical components configured to direct the at least three illumination light signals from the one or more light sources to one or more spatial points on the retina, and a light detector. The one or more optical components are also configured to direct a plurality of reflected light signals from the retina to the light detector. The light detector is configured to receive the reflected light signals as a function of intensity. The system further includes one or more processors, and one or more memory devices storing instructions. When the instructions are executed by the one or more processors, the one or more processors cause the system to generate, via the one or more light sources, a first set of the at least three illumination light signals, detect, via the light detector, the reflected light signals in response to the generation of the first set of the at least three illumination signals, and determine a first opsin density using the detected intensity of the reflected light signals.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 3 is a graphical illustration of an exemplary timing scheme for actuating one or more light sources and a light detector according to some aspects of the present disclosure.

FIG. 4A is a photographic image of a retina during a fully dark-adaptive time period of an experiment.

FIG. 4B is a photographic image of the retina during a photobleaching event of the experiment of FIG. 4A.

FIG. 4C is a photographic image of the retina during after the photobleaching event of FIG. 4B.

FIG. 4D graphically illustrates experimental data of rhodopsin densities over time for the experiment.

FIG. 4E illustrates a mapping of the rhodopsin density on an image of the retina of the test subject of the experiment.

FIG. 4F illustrates a mapping of the regeneration speed of rhodopsin onto an image of the retina of the test subject of the experiment.

Figure 1:
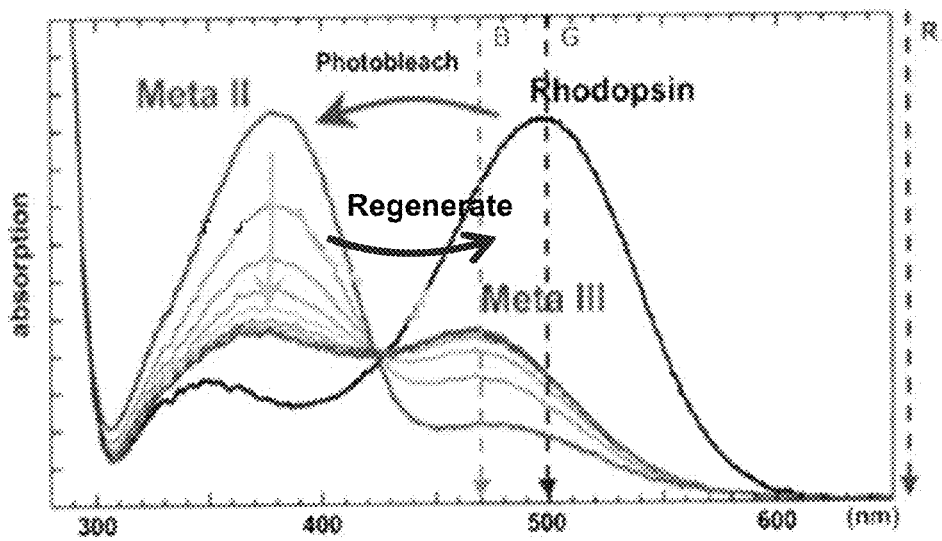
FIG. 1 is a graphical illustration of the spectral signatures for rhodopsin, metarhodopsin II, and metarhodopsin III for an exemplary visual cycle.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

According to aspects of the present disclosure, systems and methods employ imaging multispectral reflectometry to directly, quantitatively, and noninvasively map the density and regeneration speed of functional photopigment (e.g., opsins such as rhodopsin and photopsins) to facilitate assessment of the functionality and health of the photoreceptor and the retinal pigment epithelial cells in vivo. By obtaining the density and regeneration speed of the functional photopigment, research, classification, diagnosis, treatment and patient management in connection with a number of retinal diseases can be advanced. Indeed, the systems and methods of the present disclosure provide quantitative criteria for retinal health (i.e., the density and regeneration speed of functional photopigment) not previously determined.

In contrast to other techniques for assessing characteristics of a retina, the imaging multispectral reflectometry systems and methods of the present disclosure use light to probe the aspects of the visual cycle that are specifically and directly connected with the health and functionality of the photoreceptor and retinal pigment epithelium cells. When an illumination light signal is incident on the retina, a portion of the incident light is absorbed by the functional opsin and a portion of the incident light is reflected from the retina. The amount of light reflected from the retina is based, at least in part, on the density of the functional opsin in the retina. Thus, the density of the functional opsin in the retina can be determined based on detection and analysis of light reflected from the retina.

Additionally, after photobleaching, the bleached opsin has to be replenished by the 11-cis retinal molecules that are supplied by the retinal pigment epithelium cells to the photoreceptor cells in vivo before the opsin becomes functional again and can absorb new light. Measurements of reflected light during dark adaption after a photobleaching event can be used to determine the rate at which the density of the opsin increases, which is indicative of the regeneration speed of the opsin. The regeneration of opsin during dark adaption can be used to assess the functional relationship between the photoreceptor cells and the supporting retinal pigment epithelium cells. Thus, the multispectral reflectometry techniques of the present disclosure provide a direct means to assay the density and regeneration speed of the functional opsin of the retina and assess the health of the photoreceptor cells and the retinal pigment epithelium cells in intact eyes.

The basis for aspects of the present disclosure is the Beer-Lambert law. According to the Beer-Lambert law, the intensity of a light signal reflected from the retina, $I_{Out}$ can be determined based on a calculation having the general form of the following equation:

$$I_{Out}(x,y,\lambda,t) = I_{In}(x,y,\lambda)10^{-[n_R(x,y,t)\epsilon_R(\lambda)+n_0(x,y)\epsilon_0(\lambda)]} \quad \text{eq.(1)}$$

where $I_{In}(x, y, \lambda)$ is the intensity of an illumination light incident on the retina, $\lambda$ is a wavelength of the illumination light, t is a time point, (x, y) is a spatial point, $n_R(x, y, t)$ is the area density of the opsin at the time point t and the spatial point (x,y), $\epsilon_R(\lambda)$ is the molar absorptivity of the opsin at the wavelength $\lambda$, $n_0(x, y)$ is the mean area density of all relatively fixed pigments (e.g., melanin) at the spatial point (x,y), and $\epsilon_0(\lambda)$ is the moloar absorptivity of all relatively fixed pigments (e.g., melanin) at the wavelength $\lambda$.

Equation (1) can also be expressed, according to an image reflectometry convention, in terms of double-pass optical densities (e.g., $D_R(x, y, \lambda, t) = n_R(x, y, t)\epsilon_R(\lambda)$) as a calculation having the general form of the following equation:

$$I_{Out}(x,y,\lambda,t) = P_{In}(\lambda)c(x,y,t)10^{-[D_R(x,y,\lambda,t)+D_0(x,y,\lambda)]} \quad \text{eq. (2)}$$

where $P_{In}(\lambda)$ is a power of the illumination light signal at wavelength $\lambda$, c(x, y, t) is a lump optics factor that characterizes the time varying illumination pattern and detection efficiency of an image capture device caused by the constantly moving eye ball, and $D_R(x, y, \lambda, t)$ and $D_0(x, y, \lambda)$ are the double-pass optical densities of the opsin, and the other relatively photo-stable pigments (e.g. melanin) respectively. The double-pass optical density of each type of pigment is directly related to the number of the corresponding pigment molecules per unit area through its molar absorptivity. For example, a double-pass optical density of 0.35 for rhodopsin at 500 nm corresponds to a density of 4.3 nmol/cm² rhodopsin molecules on the retina. For purposes of the present detailed description, the term "density" is used to refer to the double-pass optical density.

When the retina is fully bleached by the incident light, no opsin exists in the retina (i.e., $n_R(x, y, t)=0$). Thus, at the time point when the retina is fully bleached by the incident light, $t_{bleached}$, the intensity of the reflected light can be determined based on a calculation having the general form of the following equation:

$$I_{Out}(x,y,\lambda,t_{bleached}) = I_{In}(x,y,\lambda)10^{-[n_0(x,y)\epsilon_0(\lambda)]} \quad \text{eq. (3)}$$

Therefore, in view of equations (1)-(3), the opsin density $D_R(x, y, t)$ can be determined based on a calculation having the general form of the following equation:

$$D_R(x, y, t) = -\log_{10}\frac{I_{Out}(x, y, \lambda, t)}{I_{Out}(x, y, \lambda, t_{bleached})} \quad \text{eq. (4)}$$

In other words, the opsin density on the retina at a point in time, t, can be quantitatively determined based on a ratio between the reflected light intensity at the point in time, t, and the reflected light intensity at the point in time when the retina is fully bleached, $t_{bleached}$.

The above approach for determining the density of the opsin is based on the use of an illumination light having a single wavelength. Significantly, however, when the opsin density is determined based on the calculation having the general form of equations (1)-(4), the determination fails to account for one or more substantial interfering effects. In particular, for example, metarhodopsin III is a transient byproduct from the decomposition of rhodopsin, generated by the bleaching from the illumination light incident on the retina. Metarhodopsin III also absorbs illumination light incident on the retina, albeit according to a different spectral absorption signature. For example, FIG. 1 illustrates a plurality of spectral signatures for rhodopsin, metarhodopsin II, and metarhodopsin III for a visual cycle. As shown in FIG. 1, due to the substantial spectral overlapping between metarhodopsin III and rhodopsin, accurate measurement of the rhodopsin density and the rhodopsin regeneration is prohibited without accounting for the density of the metarhodopsin. Thus, the single wavelength approach cannot provide sufficient accuracy.

Figure 2:
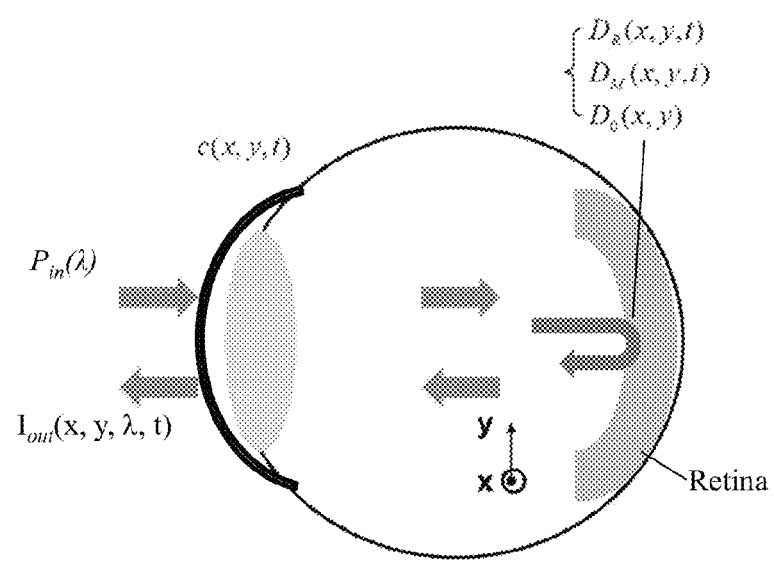
FIG. 2 is a graphical illustration of an equation for determining the density of an opsin according to some aspects of the present disclosure.

It has been discovered that the application of imaging multispectral techniques utilizing illumination lights having at least three wavelengths permits rapid and reliable determination of opsin density and regeneration for each class of photoreceptor cells, while accounting for significant interfering effects such as metarhoposin III and the movement of a patient's eye. According to aspects of the present disclosure, a diagnostic process to assess the health and functionality of the retina includes at least three measurements at different wavelengths utilizing a calculation having the general form of the following equation:

$$I_{Out}(x,y,\lambda,t) = P_{In}(\lambda)c(x,y,t)$$
$$10^{-[D_R(x,y,\lambda,t)+D_M(x,y,\lambda,t)+D_0(x,y,\lambda)]} \quad \text{eq.(5)}$$

where $P_{In}(\lambda)$ is the power of the illumination light signal at the wavelength $\lambda$, c(x,y,t) is the lump optics factor that characterizes the time varying illumination pattern and detection efficiency of the image capture device caused by the constantly moving eye ball, and $D_R(x, y, \lambda, t)$, $D_M(x, y, \lambda, t)$, and $D_0(x, y, \lambda)$ are the double-pass optical densities of rhodopsin, metarhodopsin III, and other relatively photo-stable pigments (e.g. melanin) respectively. A non-limiting graphical illustration of the equation (5) is illustrated in FIG. 2. While the following description is provided in terms of a rhodopsin density, it should be understood that other opsins (e.g., the photopsins of cone cells) can also be determined according to the principles disclosed herein.

Unlike the equation (2), the equation (5) includes three unknown, time-varying variables at each time point. That is, in the equation (5) the optics factor, $c(x,y,t)$, the double-pass optical density of rhodopsin, $D_R(x,y,\lambda,t)$, and the double-pass optical density of metarhodopsin III, $D_M(x, y, \lambda, t)$ are unknown. Significantly, however, the systems and methods of the present disclosure can determine these unknown variables by independently probing the retina at three different wavelengths, establishing three independent equations having the general form of the equation (5), and solving for the unknown time varying variables. For example, the equation (5) can be expressed for each of the at least three illumination light signals as follows:

$$\begin{cases} I_{Out}(x, y, \lambda_1, t) = P_{In}(\lambda_1)c(x, y, t)10^{-\left[\frac{D_R(x,y,\lambda_1,t)+D_M(x,y,\lambda_1,t)+}{D_0(x,y,\lambda_1)}\right]} \\ I_{Out}(x, y, \lambda_2, t) = P_{In}(\lambda_2)c(x, y, t)10^{-\left[\frac{D_R(x,y,\lambda_2,t)+D_M(x,y,\lambda_2,t)+}{D_0(x,y,\lambda_2)}\right]} \\ \vdots \\ I_{Out}(x, y, \lambda_n, t) = P_{In}(\lambda_n)c(x, y, t)10^{-\left[\frac{D_R(x,y,\lambda_n,t)+D_M(x,y,\lambda_n,t)+}{D_0(x,y,\lambda_n)}\right]} \end{cases} \quad \text{eqs. (6)}$$

where n is the number of illumination light signals, $\lambda_1$ is the wavelength of the first illumination light signal, $\lambda_2$ is the wavelength of the second illumination light signal, and $\lambda_n$ is the wavelength of the nth illumination light signal. Using the equations (6), the double-pass optical density of rhodopsin, $D_R(x,y,\lambda,t)$, the double-pass optical density of metarhodopsin III, $D_M(x, y, \lambda, t)$, and the optics factor, $c(x,y,t)$, can be determined for a particular spatial point, wavelength, and time point. As such, the double-pass optical density of rhodopsin at a particular point in time, a particular point in space and a particular wavelength can be determined independent of interfering effects such as the metarhodopsin III density and the optics factors (e.g., eye movement). Advantageously, clinically relevant information can be extracted from one or more double-pass optical density of rhodopsin measurements to assess the function and health of the retina.

More particularly, at least two quantitative and clinically-relevant pieces of information can be extracted from the rhodopsin density measurement determined from the equations (6). First, the density of the functional rhodopsin, $\Delta D_R(x, y)$, can be determined based on the change in rhodopsin density between a time when the retina is fully dark-adaptive, $t_{dark}$, (i.e., a time when all or substantially all functional rhodopsin is recovered and the retina absorbs the most light) and a time when the retina is fully bleached, $t_{bleached}$ (i.e., a time when no or negligible functional rhodopsin exists and the retina reflects the most light). The density of functional rhodopsin, $\Delta D_R(x, y)$, is different from the time varying rhodopsin density, $D_R(x, y, \lambda, t)$, in that the density of functional rhodopsin is an indication of the maximum rhodopsin density capacity. The density of functional rhodopsin provides an indication of the sensitivity of the photoreceptor cells to receiving light signals. The functional rhodopsin density, $\Delta D_R(x, y)$, can be determined by a calculation having the general form of the following equation:

$$\Delta D_R(x, y) = \quad \text{eq. (7)}$$
$$D_R(x, y, t_{Dark}) - D_R(x, y, t_{bleach}) = -\log_{10} \frac{I_{Out}(x, y, \lambda, t_{Dark})}{I_{Out}(x, y, \lambda, t_{bleach})}$$

Second, the regeneration speed of the rhodopsin, $k(x, y)$, can be determined by taking additional measurements of the time varying rhodopsin density, $D_R(x, y, \lambda, t)$, after a bleaching event. Indeed, after a bleaching event, the retinal pigment epithelium cells will provide 11-cis retinal to the photoreceptor cells, regenerating the density of rhodopsin within the retina. The regeneration speed of rhodopsin provides an indication of the capability of the retinal pigment epithelium cells to provide nutrients to the photoreceptor cells and recover their vision functionality. As a result of the substantially improved accuracy of the imaging multispectral reflectometry approach utilizing at least three wavelengths, it has been discovered that the regeneration speed of rhodopsin is substantially linear. Thus, taking one or more additional measurements at a time(s) after the retina is fully bleached, $t_{postbleached}$, the regeneration speed of the rhodopsin, $k(x, y)$, can be determined based on a calculation having the general form of the following equation:

$$k(x, y) = \frac{D_R(x, y, t_{postbleached})}{t_{postbleached} - t_{bleached}} = \frac{D_R(x, y, t + \Delta t) - D_R(x, y, t)}{\Delta t} \quad \text{eq. (8)}$$

To demonstrate the quantitative and noninvasive nature of the imaging multispectral reflectometry approach of the present disclosure, an exemplary experiment was performed. First, the test subject was kept in a dark environment for a period of time suitable to allow its retina to be fully dark-adapted and all of the rhodopsin molecules to be in a regenerated state (e.g., approximately 12 hours). Then, during an initial ten minute period, the test subject's retina was exposed to illumination light signals having a weak intensity at three different wavelengths and the resulting light signals reflected from the retina were measured by a light detector (e.g., a charge-coupled device also known as a CCD camera). In particular, the illumination light signals included a red light signal having a wavelength of 660 nm and an intensity of 16 µW, a blue light signal having a wavelength of 470 nm and an intensity of 26 µW, and a green light signal having a wavelength of 500 nm and an intensity of 21 µW (all having a 10 nm bandwidth).

The illumination light signals were applied in sets to the retina as illustrated, for example, in FIG. 3. Each set included three illumination light signals, one for each wavelength. The duration of each illumination light signal and the light detector exposure time was 30 milliseconds. The resting time between each illumination light signal in a set was 15 milliseconds. The resting time between each set of illumination light signals was 120 seconds.

After the initial ten minute time period, a separate green photobleaching light having a wavelength of 505 nm at an intensity of 135 µW (and a 29 nm bandwidth) was applied for 26 seconds to deeply and selectively photobleach most of the rhodopsin (e.g., greater than 95% bleached) on the retina. The photobleaching event initiated a regeneration of the rhodopsin. During a 40 minute time period after the photobleaching event, the weak illumination light at the three wavelengths was again used at the exposure and resting times described above to monitor the regeneration of the photo-absorbing rhodopsin and the recovery of the retina's visual function in the dark.

FIG. 4a illustrates an image of the retina during the initial ten minute time period when the retina was fully dark-adapted and absorbs the most amount of light. FIG. 4b illustrates an image of the retina when the retina was deeply photobleached and absorbs the least amount of light. FIG. 4c illustrates an image of the retina during the forty minute time period when the retina had recovered some of its capability to absorb light.

Based on the measurements obtained during the initial ten minute time period and the subsequent 40 minute time period, the rhodopsin density was determined using the single wavelength approach and using the multispectral wavelength approach of the present disclosure. To better illustrate the absorbance change of the retina at the absorption maximum of rhodopsin, an image of the retina was divided into a 3×3 grid as shown in FIGS. 4a-4c. FIG. 4d illustrates a plot for each of the grid segments of the mean optical density at the 500 nm wavelength. The data determined for the single wavelength approach (indicated in grey in FIG. 4d) is based on calculations using equation (4) as follows:

$$D_R(x, y, \lambda_{500}, t) = -\log_{10} \frac{I_{Out}(x, y, \lambda_{500}, t)}{I_{Out}(x, y, \lambda_{500}, t_{bleached})} \qquad \text{eq. (9)}$$

The data obtained for the imaging multispectral reflectometry approach of the present disclosure (indicated in black in FIG. 4d) is based on calculations using the equations (6) as follows:

$$\begin{cases} I_{Out}(x, y, \lambda_{660}, t) = P_{In}(\lambda_{660})c(x, y, t)10^{-D_0(x,y,\lambda_{660})} \\ I_{Out}(x, y, \lambda_{470}, t) = P_{In}(\lambda_{470})c(x, y, t)10^{-\begin{bmatrix} D_R(x,y,\lambda_{470},t)+ \\ D_M(x,y,\lambda_{470},t)+ \\ D_0(x,y,\lambda_{470}) \end{bmatrix}} \\ I_{Out}(x, y, \lambda_{500}, t) = P_{In}(\lambda_{500})c(x, y, t)10^{-\begin{bmatrix} D_R(x,y,\lambda_{500},t)+ \\ D_M(x,y,\lambda_{500},t)+ \\ D_0(x,y,\lambda_{500}) \end{bmatrix}} \end{cases} \qquad \text{eqs. (10)}$$

where $P_{In}(\lambda)$ is the power of the illuminating light source at relevant wavelength $\lambda$, $c(x, y, t)$ is a lump optics factor, and $D_R(x, y, \lambda, t)$, $D_M(x, y, \lambda, t)$, and $D_0(x, y, \lambda)$ are the double-pass optical densities of rhodopsin, metarhodopsin III, and other relatively photo-stable pigments (e.g. melanin) respectively. Because the rhodopsin and the metarhodopsin III do not absorb light at the 660 nm wavelength, the $D_R(x, y, \lambda_{660}, t)$ and $D_M(x, y, \lambda_{660}, t)$ are 0 and, thus, not included in the equations (10). Solving the equations (10) for the double-pass optical density of rhodopsin at 500 nm, $D_R(x, y, \lambda_{500}, t)$, the experimental data illustrated in FIG. 4d for the imaging multispectral reflectometry approach was determined according to a calculation using the following equation:

$$D_R(x, y, \lambda_{500}, t) = \frac{-\log_{10}\left[\frac{\frac{I_{Out}(x, y, \lambda_{500}, t)}{I_{Out}(x, y, \lambda_{660}, t)}}{\frac{I_{Out}(x, y, \lambda_{500}, t_{bleached})}{I_{Out}(x, y, \lambda_{660}, t_{bleached})}}\right] + \frac{\varepsilon_M(\lambda_{500})}{\varepsilon_M(\lambda_{470})}\log_{10}\left[\frac{\frac{I_{Out}(x, y, \lambda_{470}, t)}{I_{Out}(x, y, \lambda_{660}, t)}}{\frac{I_{Out}(x, y, \lambda_{470}, t_{bleached})}{I_{Out}(x, y, \lambda_{660}, t_{bleached})}}\right]}{\left[1 - \frac{\varepsilon_M(\lambda_{500})\varepsilon_R(\lambda_{470})}{\varepsilon_M(\lambda_{470})\varepsilon_R(\lambda_{500})}\right]} \qquad \text{eq. (11)}$$

where $\varepsilon_M(\lambda_{500})/\varepsilon_M(\lambda_{470})=0.77$ is the ratio of the molar absorptivity of metarhodopsin III at 500 nm and 470 nm, $\varepsilon_R(\lambda_{470})/\varepsilon_R(\lambda_{500})=0.72$ is the ratio of the molar absorptivity of rhodopsin at 470 nm and 500 nm, and $I_{Out}(x, y, \lambda, t_{bleached})$ is the reflected light image of the deeply photobleached retina at wavelength $\lambda$ where little rhodopsin molecules exist.

From the results illustrated in FIG. 4d, it can be seen that the density measurement using a single wavelength approach (shown in grey in FIG. 4d) may be informative about the status of the retina; however, the irregularity of the results shows the interferences from the transient response of metarhodopsin III and eye movement, which prohibits drawing quantitative conclusions. By contrast, as shown in FIG. 4d, the measurements of the density of rhodopsin, $D_R(x, y, \lambda_{500}, t)$, obtained by the imaging multispectral reflectometry approach of the present disclosure (shown in black in FIG. 4d) are free of such interferences. Additionally, from the experimental results illustrated in FIG. 4d, it can be seen that the regeneration of the rhodopsin is linear for the imaging multispectral reflectometry approach but no such linear relationship is exhibited by the single wavelength approach data due to the irregularity of data failing to account for interring effects.

Accordingly, while the irregularity of data determined the single wavelength approach prohibits quantitative analysis, the data determined by the imaging multispectral reflectometry approach shown in FIG. 4d illustrates that clinically relevant information can be extracted to assess the function and health of the retina. Thus, the imaging multispectral reflectometry approach of the present disclosure is superior to the single wavelength approach.

For example, as shown in FIG. 4d, the density of the rhodopsin of a fully dark-adapted can be determined according to the equation (7) (i.e., $\Delta D_R(x, y)=D_R(x, y, \lambda_{500}, t_{Dark})$, where 0 minutes$<t_{Dark}<$10 minutes) to provide an indication of the sensitivity of the photoreceptor cells to receive light signals. In other words, the maximum density of the rhodopsin that is available for visual light (i.e., absorbing light) was measured over the initial ten minute time period. Information in connection with the density of the rhodopsin can also be represented by mapping the density values onto an image of the retina. For example, FIG. 4e illustrates a 147×105 pixel resolution map of the density of rhodopsin over a 35°×25° field-of-view of the retina.

Additionally, for example, as shown in FIG. 4d, the slope of the density of rhodopsin during the regeneration of the retina can be determined according to equation (8) (i.e., k(x, y)=

$$\frac{D_R(x, y, \lambda_{500}, t+\Delta t) - D_R(x, y, \lambda_{500}, t)}{\Delta t},$$

where 10 minutes$<t<$50 minutes) to provide an indication of the capability of the retinal pigment epithelium cells to provide nutrients to the photoreceptor cells and recover their visual functionality. Information in connection with the regeneration speed of the rhodopsin can also be visually represented by mapping the density values onto an image of the retina. For example, FIG. 4f illustrates a 147×105 pixel resolution map of the regeneration speed of rhodopsin over a 35°×25° field-of-view of the retina.

The above-described experiment is a non-limiting example of a process for analyzing the health and functionality of the retina. It is contemplated that, according to aspects of the present application, a method for analyzing the health and functionality of the retina may omit aspects of the above experiment, include additional aspects not described for the experiment, and/or modify the aspects of the experiment described above. For example, it is contemplated that more than three illumination light sources can be utilized. Additionally, while the above experiment was conducted to determine quantitative data relating to the rhodopsin within the retina, it is contemplated that, according to additional or alternative aspects, the process employed during the experiment can be utilized to determine quantitative data relating to other opsins such as, for example, a photopsin in a cone photoreceptor cell.

As yet another example, in the above experiment, the illumination light sources were selected to include a wavelength at 470 nm, a wavelength at 500 nm, and a wavelength at 660 nm. While, according to alternative aspects, illumination light sources operating at different wavelengths can be utilized, the particular wavelengths utilized during the experiment were selected to address specific considerations. Referring back to FIG. 1, a plurality of spectral signatures for rhodopsin, metarhodopsin II, and metarhodopsin III are illustrated for the visual cycle. As shown in FIG. 1, rhodopsin has a maximum absorption at 500 nm, metarhodopsin III has maximum absorption at 470 nm, and neither rhodopsin nor metarhodopsin III is absorbed at 660 nm. Measuring at the absorption maximums for rhodopsin and metarhodopsin III advantageously yields results having a high signal-to-noise ratio. As explained above, because no light is absorbed by rhodopsin or metarhodopsin III at 660 nm, measuring at a wavelength of 660 nm simplifies the determination of the rhodopsin density when solving the equations (7) (as demonstrated by the equation (10) and the equation (11)).

Figure 5:
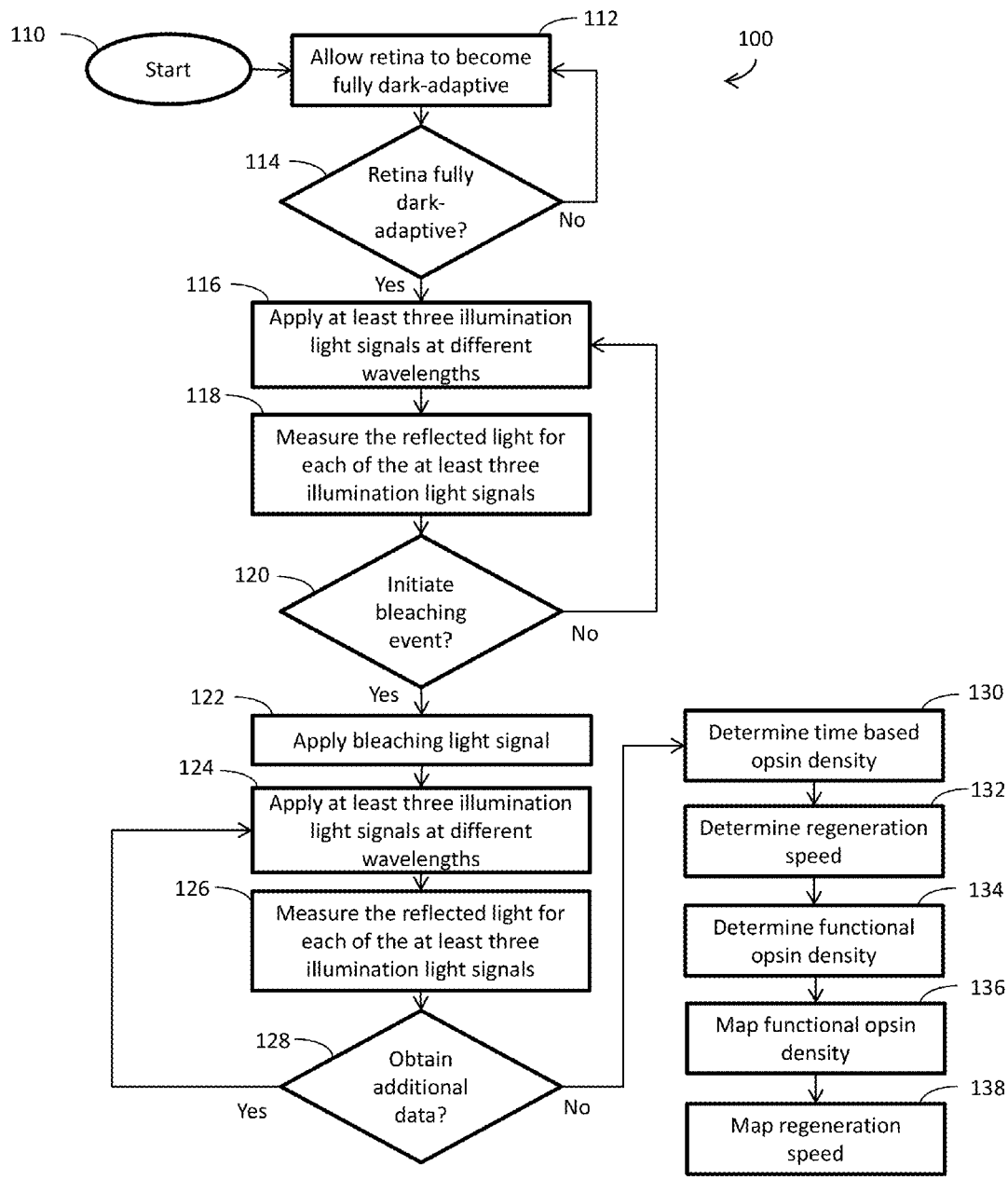
FIG. 5 is a flowchart of an exemplary process for noninvasive analysis of a retina according to some aspects of the present disclosure.

Referring now to FIG. 5, an exemplary flowchart for a method 100 of conducting an analysis of the retina using the imaging multispectral reflectometry approach of the present disclosure is illustrated. At block 110, the process 100 is initiated. At block 112, the retina is permitted to become fully dark-adaptive (i.e., all or substantially all functional rhodopsin is recovered). According to some aspects of the present disclosure, the patient's retina can be exposed to dark conditions for a suitable time period such as, for example, a time period in the range of approximately 30 minutes to approximately 24 hours. At block 114, it is determined whether the retina has become fully dark-adaptive. For example, this determination can be based on whether a predetermined amount of time has expired since the retina was first exposed to the dark conditions. If it is determined, at block 114, that the retina has not yet become fully dark-adaptive, the process 100 returns to block 112. On the other hand, if it is determined, at block 114, that the retina has become fully dark-adaptive, the process 100 proceeds to the block 116.

At block 116, the retina is exposed to at least three illumination light signals having different wavelengths. The wavelengths of the at least three illumination light signals can include any wavelengths within the visible spectrum. According to one non-limiting example, a first of the at least three illumination light signals can have a wavelength of approximately 470 nm, a second of the at least three illumination light signals can have a wavelength of approximately 500 nm, and a third of the at least three illumination light signals can have a wavelength of approximately 660 nm. According to another non-limiting example, a first of the at least three illumination light signals can have a wavelength from approximately 390 nm to approximately 500 nm, a second of the at least three illumination light signals can have a wavelength from approximately 470 nm to approximately 550 nm, and a third of the at least three illumination light signals can have a wavelength of from approximately 600 nm to approximately 700 nm. Additionally, according to some aspects of the present disclosure, the at least three illumination light signals can have a relatively low intensity such as, for example, an intensity from approximately 10 µW to approximately 40 µW.

As a non-limiting example, each of the at least three illumination light signals can be generated by one or more light emitting diodes. Also, it is contemplated that the illumination light signals can be directed from the light emitting diodes to the retina via one or more optical components such as, for example, one or more lenses, filters, and/or mirrors. The one or more light emitting diodes can be communicatively coupled to one or more processors configured to control the generation of the at least three illumination light signals from the one or more light emitting diodes. It is contemplated that, according to some aspects, the retina can be exposed to the at least three illumination light signals as a set of illumination light signals having a predetermined exposure time for each illumination light signal within the set, a rest time between illumination light signals within the set, and a rest time between successive sets. As a non-limiting example, the exposure time of an illumination light signal can be approximately 5 milliseconds to approximately 60 milliseconds, a resting time between illumination light signals of a set of approximately 5 milliseconds to approximately 60 milliseconds, and a resting time between successive sets of approximately 30 seconds to approximately 500 seconds.

At block 118, the light reflected from the retina in response to the exposing the retina to the at least three illumination light signals is detected by a light detector. The light detector can be communicatively coupled to one or more processors configured to receive and process one or more electrical signals from the light detector that are indicative of the reflected light detected by the light detector.

At block 120, it is determined whether a photobleaching event should be initiated. For example, at least one of the one or more processors can determine that a photobleaching event should be initiated based on whether a predetermined amount of time has expired since it was determined that the retina was fully dark-adaptive (i.e., at block 114) or since an initial illumination light signal was applied to the retina (i.e., at block 116). While the photobleaching event was initiated after ten minutes in the above-described experiment, it is contemplated that any other time period can be utilized. As another example, it can be determined that a photobleaching event should be initiated based on the number of reflected light signals detected by the light detector at block 118. If it is determined, at block 120, that a photobleaching event should not be initiated, then the process 100 returns to block 116 to apply additional illumination light signals to the retina and measure the resulting reflected light (at block 118). On the other hand, if it is determined, at block 120, that a photobleaching event should be initiated, then the process 100 proceeds to block 122.

At block 122, the retina is exposed to a photobleaching light signal to photobleach the retina. According to aspects of the present disclosure, the photobleaching light signal can have any wavelength, intensity, and exposure time that are suitable to photobleach the retina. As one non-limiting example, the photobleaching light can have a wavelength of approximately 505 nm, an intensity of approximately 135 µW, and exposure time from approximately 15 seconds to approximately 120 seconds. As another non-limiting example, the photobleaching light can be a white light.

At block 124, the retina is again exposed to the at least three illumination light signals having different wavelengths in manner similar to that described above with respect to block 116. Likewise, at block 126, the reflected light signals received from the retina are detected by the light detector in a manner similar to that described above with respect to the block 118. At block 128, it is determined whether additional data should be obtained (i.e., whether additional illumination light signals should be generated and reflected light signals detected). For example, at least one of the one or more processors can determine whether additional data should be obtained based on whether a predetermined amount of time has expired since it was determined that the retina was fully dark-adaptive (i.e., at block 114), since an initial illumination light signal was applied to the retina (i.e., at block 116), since the photobleaching event occurred (i.e., at block 122). As another example, it can be determined whether additional data should be obtained based on the number of reflected light signals detected by the light detector at block 126. If it is determined, at block 128, that additional data should be obtained, the process 100 returns to the block 124. On the other hand, if it is determined, at block 128, that additional data should not be obtained, then the process 100 proceeds to block 130.

At block 130, the time based opsin density is determined based on the reflected light signals measured by the light detector at the blocks 118 and 126 based, at least in part, on the equations having the general form of the equation (6). At block 132, the regeneration speed of the opsin is determined based, at least in part, on the equations having the general form of the equation (7). At block 134, the functional opsin density is determined based, at least in part, on the equation having the general form of the equation (8). According to some aspects of the present disclosure, the determinations of blocks 130, 132, 134 can be made for one or more of the wavelengths of the at least three illumination signals. At block 136, the functional opsin density can be mapped for an image of the retina. At block 138, the regeneration speed of the opsin can be mapped for an image of the retina. It is further contemplated that, according to some aspects, the determinations of blocks 130, 132, 134 and the mappings at blocs 136, 138 can be performed by at least one of the one or more processors in communication with the light detector.

FIG. 5, described by way of example above, represents an exemplary algorithm that corresponds to at least some instructions executed by one or more processors to perform the above described functions associated with the disclosed concepts. It is also within the scope and spirit of the present concepts to omit steps, include additional steps, and/or modify the order of steps presented above.

Figure 6:
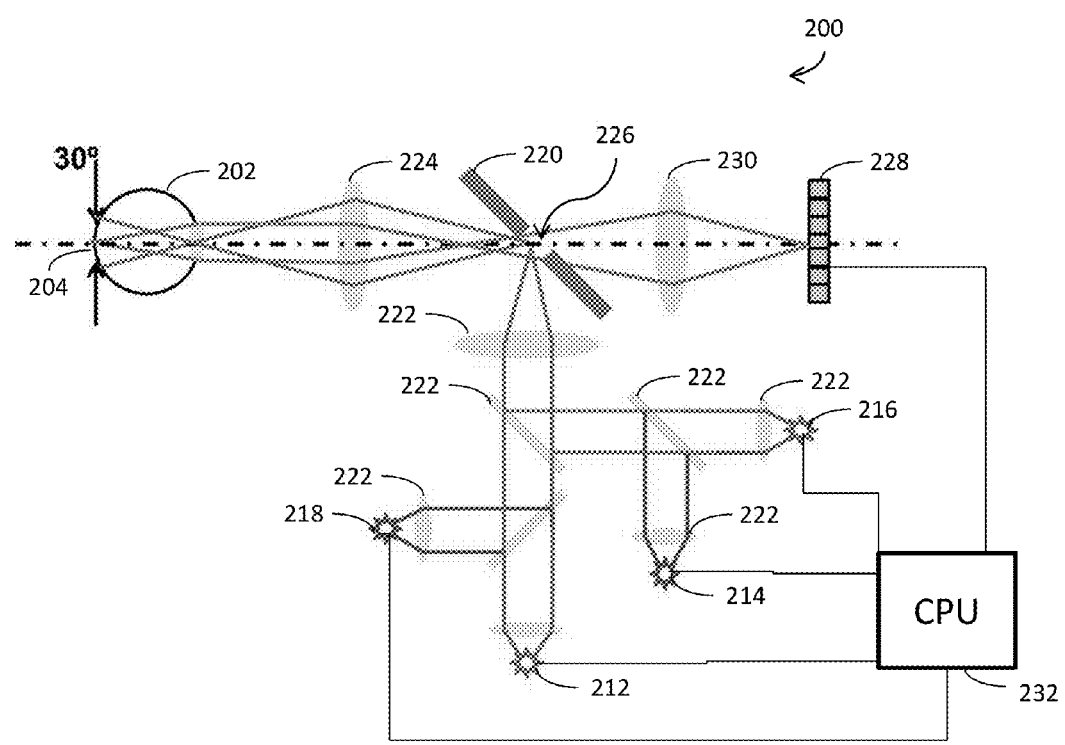
FIG. 6 is a schematic of an exemplary system for noninvasive analysis of a retina according to some aspects of the present disclosure.

Referring now to FIG. 6, a schematic illustration of a non-limiting example of a system 200 for performing a imaging multispectral reflectometry approach is shown. The system 200 includes a first light source 212, a second light source 214, and a third light source 216. The first light source 212, the second light source 214, and the third light source 216 are each configured to generate an illumination light signal at a different wavelength. For example, the first light source 212, the second light source 214 and the third light source 216 can include one or more light emitting diodes and/or other light sources configured to generate a light signal having a different wavelength in the visible spectrum. In the device used in the experiment described above, the first light source 212, the second light source 214, and the third light source 216 were light emitting diodes having model numbers M660L2, M505L1, and M470L2 manufactured by Thorlabs Inc., which is presently headquartered at 56 Sparta Avenue, Newton, N.J. 07860.

The system 200 further includes a photobleaching light source 218 that is configured to generate a photobleaching light signal at a wavelength, an intensity, and for an exposure time that are suitable to photobleach the retina 204 of the eye 202. For example, the photobleaching light source 218 can also include one or more light emitting diodes and/or other light sources.

The first light source 212, the second light source 214, the third light source 216 and the photobleaching light source 218 are optically coupled to an annulus mirror 220 via one or more optical components 222 (e.g., one or more of a lens, a mirror, a filter, a fiber optic cable, a light guide, etc.). For example, in the experiment described above, the first light source 212, the second light source 214, and third light source 216 were optically coupled to the annulus mirror 220 via 10 nm bandpass filters having model numbers FB660-10, FB500-10, and FB470-10 M470L2 manufactured by Thorlabs Inc., which is presently headquartered at 56 Sparta Avenue, Newton, N.J. 07860. The annulus mirror 220 is configured to direct light from the first light source 212, the second light source 214, the third light source 216, and/or the photobleaching light source 218 to the retina 204. The system 200 can optionally include one or more optical components 224 located between the annulus mirror 220 and the eye 202 to assist in directing the light from the annulus mirror 220 on to one or more spatial points of the retina 204.

The annulus mirror 220 includes an aperture 226 that is configured to permit light reflected from the retina 204 to pass through the annulus mirror 220 and be received by a light detector 228. The system 200 can also optionally include one or more optical components 230 located between the annulus mirror 220 and the light detector 228 to assist in directing the light reflected from the retina 204 on to the light detector 228. The light detector 228 is configured to detect the reflected light as a function of intensity and convert the detected reflected light into an electrical signal that can be processed by one or more processors 232. One example of a light detector is a charge coupled device ("CCD"). In the experiment described above, for example, the light detector was an image camera having a model number DVC-1500M manufactured by DVC Company, which is presently headquartered at 4120 Freidrich Lane, Suite M-500, Austin, Tex. 78744.

The one or more processors 232 are communicatively coupled to the light detector, the first light source, the second light source, the third light source, and the photobleaching light source to facilitate control and synchronization of the light detector, the first light source, the second light source, the third light source, and the photobleaching light source. More generally, the one or more processors 232 comprise any combination of hardware, software, or firmware configured to control and execute the methods and processes disclosed herein. The hardware aspects may include combinations of operatively coupled hardware components including microprocessors, logical circuitry, communication/networking ports, digital filters, memory, or logical circuitry. The one or more processors 232 may be adapted to perform operations specified by a computer-executable code, which may be stored on a computer readable medium.

As described above, the one or more processors 232 may be a programmable processing device, such as an external conventional computer or an on-board field programmable gate array (FPGA) or digital signal processor (DSP), that executes software, or stored instructions. In general, physical processors 232 and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the exemplary embodiments of the present disclosure, as is appreciated by those skilled in the computer and software arts. The physical processors and/or machines may be externally networked with the image capture device(s), or may be integrated to reside within the light detector. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the exemplary embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

As a non-limiting example, the one or more processors 232 utilized during the above described experiment included a D/A card having a model number PCI-6713 manufactured by National Instrument Company, which is presently headquartered at 11500 North Mopac Expressway, Austin, Tex. 78759.

It is contemplated that, according to some aspects of the present disclosure, the system 200 can further include an eye positioning system (not shown) configured to position the retina of a patient relative to the annulus mirror and/or other optical components of the system. For example, the system 200 can include a fundus camera modified to include one or more of the features (e.g., the at least three illumination light sources) of the system 200 described above.

It is also within the scope and spirit of the present concepts to omit features, include additional features, and/or modify the features presented for FIG. 6 above. For example, while the system 200 described and illustrated above with respect to FIG. 6 includes a first light source 212, a second light source 214, and a third light source 216 configured to probe a retina 204, according to additional or alternative aspects of the present disclosure, the system 200 can include more than three light sources for probing the retina 204. Additionally, it is contemplated that the system 200 can omit the photobleaching light source 218 if, for example, the system is not configured to determine a regeneration speed of an opsin.

While the system 200 described and illustrated for FIG. 6 can utilize full-field imaging techniques in which the reflected light intensity at each spatial point on the retina was measured with a single snap shot, according to alternative aspects of the present disclosure, the imaging multispectral reflectometry approach of the present disclosure can be employed using a scanning laser ophthalmoscopy system and method as well. In a scanning laser ophthalmoscopy system and method, a plurality of snap shots are taken under each wavelength independently using, for example, a raster-scan scheme to probe each spatial point on the retina, one after another. This technique allows the focused illumination light to remain on each spatial point for a predetermined amount of time. As such, the predetermined time period can be utilized to multiplex the wavelengths. According to some aspects, a time domain multiplexing scheme can be utilized (e.g., turn on each wavelength sequentially). According to other aspects, a frequency domain multiplexing scheme can be utilized (e.g., modulate each wavelength with a different frequency).

Figure 7:
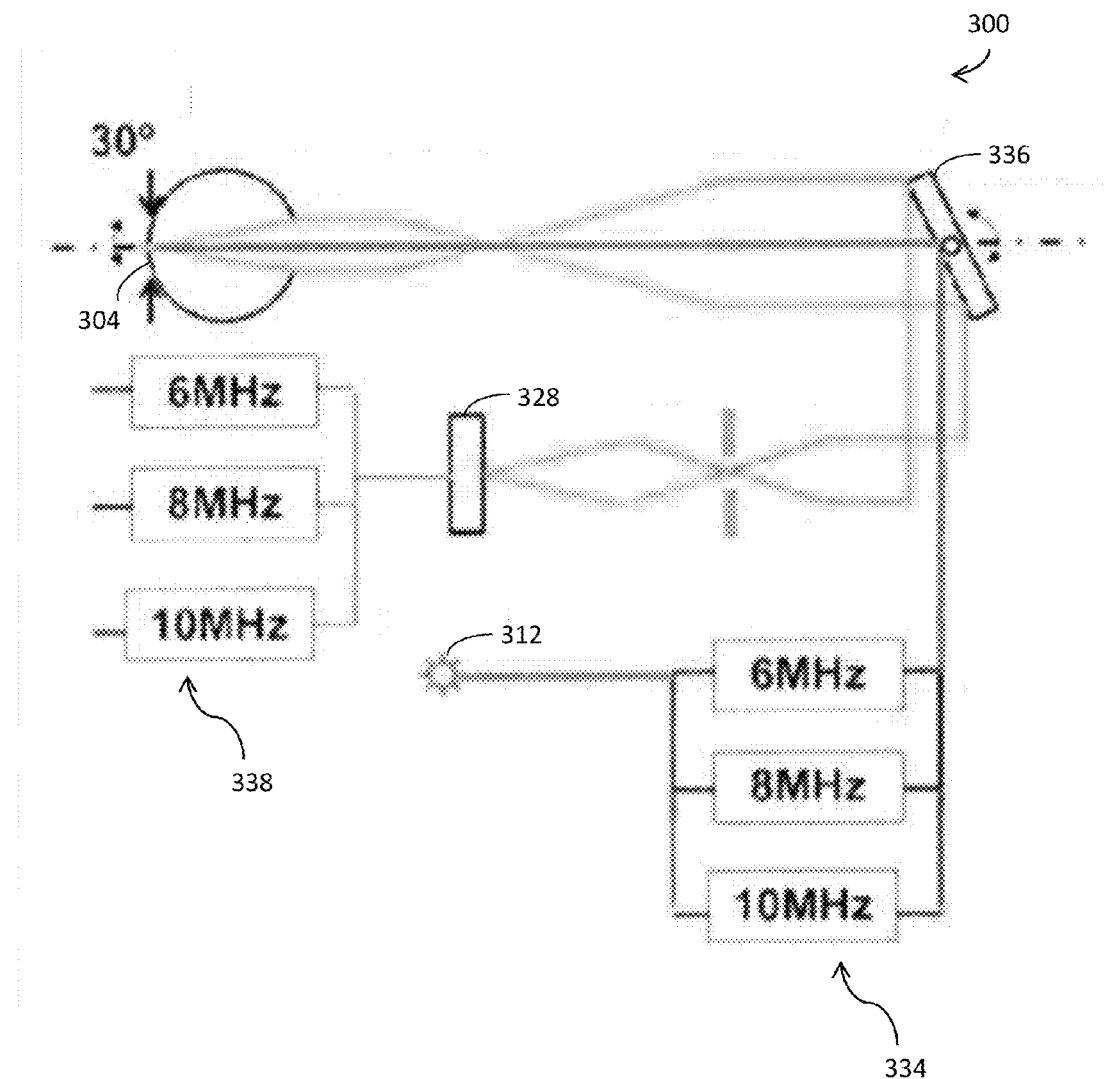
FIG. 7 is a schematic of an exemplary system for noninvasive analysis of a retina according to additional or alternative aspects of the present disclosure.

Referring to FIG. 7, a schematic illustration of a non-limiting example of a scanning laser opthalmoscopy system 300 for performing the imaging multispectral reflectometry approach of the present disclosure is shown. The system 300 includes a light source 312 that is configured to provide sufficient optical power at least three different wavelengths simultaneously. For example, the light source 312 can include an Argon/Krypton laser. The light source 312 is optically coupled to an acousto-optic modulator 334 that is configured to frequency modulate a light signal from a light source 312 according to the at least three wavelengths. As a non-limiting example, the at least three wavelengths can include approximately 488 nm, approximately 514 nm, and approximately 647 nm modulated at 6 MHz, 8 MHz, and 10 MHz, respectively. The frequency modulated light signal is directed to a retina 304 via one or more optical components 336. As a non-limiting example, the one or more optical components 336 can include a galvanometer scanner having a model number of 6215HB manufactured by Cambridge Technology, which is present headquartered at 25 Hartwell Avenue, Lexington, Mass. 02421, for the spatial point raster scanning.

The light reflected from the retina 304 in response is optically collected and directed to a light detector 328. The reflected light received by the light detector 328 can be separated into different channels, for example, by digital filtering 338 (e.g., via one or more processors), and processed according to the imaging multispectral reflectometry approach described above.

According to some aspects of the present disclosure, the at least three illumination light signals can be applied to the retina in a sequential matter, for example, as described and illustrated with respect to FIG. 3. According to additional or alternative aspects of the present disclosure, the at least three illumination light signals can be applied to the retina substantially simultaneously. To detect the at least three illumination light signal applied substantially simultaneously, it is contemplated that the light detector can include a plurality of light detectors where each light detector is configured to detect one of the at least three illumination light signal. Additionally, in one non-limiting example, the light detector can include an RGB camera configured to simultaneously detect and separate three reflected light signals received in response to three illumination light signals.

Each of these embodiments and obvious variations thereof is contemplated as falling within the spirit and scope of the claimed invention, which is set forth in the following claims.

Moreover, the present concepts expressly include any and all combinations and subcombinations of the preceding elements and aspects.

What is claimed is:

1. A method for noninvasive analysis of a retina, comprising:
    exposing the retina to one or more first sets of at least three illumination light signals generated by one or more light sources, the at least three illumination light signals each having a different wavelength;
    optically collecting a reflected light signal for each of the at least three illumination light signals of the one or more first sets, each of the reflected light signals being a portion of the respective illumination light signal reflected by the retina;
    detecting, via a light detector, the reflected light signals of the one or more first sets as a function of intensity;
    determining, via one or more processors, a first opsin density using the detected intensity of each of the reflected light signals of the one or more first sets.

2. The method of claim 1, further comprising, prior to the exposing the retina to the one or more first sets of at least three illumination light signals, exposing the retina to dark conditions for a period of time to cause full dark-adaption.

3. The method of claim 1, further comprising exposing the retina to a photobleaching light signal, the photobleaching light signal being configured to photobleach the retina.

4. The method of claim 3, further comprising:
    after the exposing the retina to the photobleaching light signal, exposing the retina to one or more second sets of the at least three illumination light signals;
    optically collecting a reflected light signal for each of the at least three illumination light signals of the one or more second sets;
    detecting, via the light sensor, the reflected light signals of the one or more second sets as a function of intensity; and
    determining, via at least one of the one or more processors, a second opsin density using the detected intensity of each of the reflected light signals of the one or more second sets.

5. The method of claim 4, further comprising determining a regeneration speed of the opsin based on at least the second opsin density.

6. The method of claim 5, wherein the regeneration speed is determined by a calculation having the general form of the following equation:

$$k(x, y) = \frac{D_R(x, y, t_{postbleached})}{t_{postbleached} - t_{bleached}}$$

where k(x,y) is the regeneration speed at a spatial point (x,y), $D_R(x,y,t_{postbleached})$ is the second opsin density at a time point $t_{postbleached}$ after the retina was exposed to the photobleaching light signal, and $t_{bleached}$ is a time point at which the retina was exposed to the photobleaching light signal.

7. The method of claim 5, wherein the determining a second opsin density comprises determining an initial and a subsequent opsin densities and the regeneration speed is determined by a calculation having the general form of the following equation:

$$k(x, y) = \frac{D_R(x, y, t + \Delta t) - D_R(x, y, t)}{\Delta t}$$

where k(x,y) is the regeneration speed at a spatial point (x,y), t is a time of the initial opsin density, $\Delta t$ is a period of time between the initial opsin density and the subsequent opsin density, $D_R(x,y,t)$ is the initial opsin density at the spatial point (x,y) and the time t, $D_R(x,y,t+\Delta t)$ is subsequent opsin density at the spatial point (x,y) and the time $t+\Delta t$.

8. The method of claim 5, wherein the regeneration speed is determined for a plurality of spatial points on the retina and the method further comprises mapping the determined regeneration speeds to the spatial points on the retina to generate an image of the retina including indications of the regeneration speeds relative to the plurality of spatial points.

9. The method of claim 1, wherein the first opsin density is determined for a plurality of spatial points on the retina and the method further comprises generating an image of the retina mapping the first opsin densities to the plurality of spatial points.

10. The method of claim 9, wherein the first opsin density is determined prior to exposing the retina to a photobleaching light source.

11. The method of claim 1, wherein the opsin is rhodopsin.

12. The method of claim 11, wherein the first opsin density is determined from a plurality of equations having the general form:

$$\begin{cases} I_{Out}(x, y, \lambda_1, t) = P_{In}(\lambda_1)c(x, y, t)10^{-\left[\frac{D_R(x,y,\lambda_1,t)+D_M(x,y,\lambda_1,t)+}{D_0(x,y,\lambda_1)}\right]} \\ I_{Out}(x, y, \lambda_2, t) = P_{In}(\lambda_2)c(x, y, t)10^{-\left[\frac{D_R(x,y,\lambda_2,t)+D_M(x,y,\lambda_2,t)+}{D_0(x,y,\lambda_2)}\right]} \\ \vdots \\ I_{Out}(x, y, \lambda_n, t) = P_{In}(\lambda_n)c(x, y, t)10^{-\left[\frac{D_R(x,y,\lambda_n,t)+D_M(x,y,\lambda_n,t)+}{D_0(x,y,\lambda_n)}\right]} \end{cases}$$

where (x,y) is a spatial point, c(x,y,t) is a lump optics factor, t is a time point, where $\lambda_1$ is the first wavelength, $I_{Out}(x,y,\lambda_1,t)$ is the intensity of the reflected light at the spatial point, the first wavelength and the time point, $P_{In}(\lambda_1)$ is the power of the illuminating light signal at wavelength $\lambda_1$, $D_R(x,y,\lambda,t)$ is the double-pass optical density of rhodopsin at the first wavelength, the spatial point and the time point, $D_M(x,y,\lambda,t)$ is the double-pass optical density of metarhodopsin III at the spatial point, the first wavelength and the time point, and $D_0(x,y,\lambda)$ is the double-pass optical density of a photo-stable pigment at the spatial point and the first wavelength, where $\lambda_2$ is the second wavelength, $I_{Out}(x,y,\lambda_2,t)$ is the intensity of the reflected light at the spatial point, the second wavelength and the time point, $P_{In}(\lambda_2)$ is the power of the illuminating light signal at wavelength $\lambda_2$, $D_R(x,y,\lambda_2,t)$ is the double-pass optical density of rhodopsin at the second wavelength, the spatial point and the time point, $D_M(x,y,\lambda_2,t)$ is the double-pass optical density of metarhodopsin III at the spatial point, the second wavelength and the time point, and $D_0(x,y,\lambda_2)$ is the double-pass optical density of a photo-stable pigment at the spatial point and the second wavelength, and where $\lambda_n$ is the nth wavelength, $I_{Out}(x,y,\lambda_n,t)$ is the intensity of the reflected light at the spatial point, the second wavelength and the time point $P_{In}(\lambda_n)$ is the power of the illuminating light signal at wavelength $\lambda_n$, $D_R(x,y,\lambda_n,t)$ is the double-pass optical density of rhodopsin at the nth wavelength, the spatial point and the time point, $D_M(x,y,\lambda_n,t)$ is the double-pass optical density of metarhodopsin III at the spatial point, the nth wavelength and the time point, and $D_0(x,y,\lambda_n)$ is the double-pass optical density of a photo-stable pigment at the spatial point and the nth wavelength.

13. The method of claim 1, wherein the exposing and the optically collecting are via a fundus camera.

14. The method of claim 1, wherein the at least three illumination light signals includes a first light signal having a wavelength of approximately 470 nm, a second light signal having a wavelength of approximately 500 nm, and a third light signal having a wavelength of approximately 660 nm.

15. The method of claim 14, wherein the intensity of the first light signal, the second light signal, and the third light signal is less than approximately 30 µW.

16. The method of claim 14, wherein the exposing the retina to the at least three illumination light sources includes exposing the retina to the first light signal, the second light signal, and the third light signal for approximately 30 milliseconds each.

17. A system for noninvasive analysis of a retina, comprising:
one or more light sources configured to generate at least three illumination light signals, each of the at least three illumination light signals having a different wavelength;
one or more optical components configured to direct the at least three illumination light signals from the one or more light sources to one or more spatial points on the retina;
an light detector, the one or more optical components further being configured to direct a plurality of reflected light signals from the retina to the light detector, the light detector being configured to receive the reflected light signals as a function of intensity;
one or more processors; and
one or more memory devices storing instructions that, when executed by the one or more processors, cause the system to:
generate, via the one or more light sources, a first set of the at least three illumination light signals,
detect, via the light detector, the reflected light signals in response to the generation of the first set of the at least three illumination signals, and determine a first opsin density using the detected intensity of the reflected light signals.

18. The system of claim 17, further comprising a photobleaching light source configured to generate a photobleaching light signal having a wavelength, an intensity, and a duration for photobleaching the retina.

19. The system of claim 18, wherein the instructions further cause the system to:
after the generation of the photobleaching light signal, generate, via the one or more light sources, a second set of the at least three illumination light signals,
detect, via the light sensor, the reflected light signals of the one or more second sets as a function of intensity; and
determine a second opsin density using the detected intensity of each of the reflected light signals of the one or more second sets.

20. The system of claim 19, wherein the instructions further cause the system to determine the regeneration speed of the opsin based on the determined second opsin density.

21. The system of claim 20, wherein the instructions further cause the system to map the regeneration speed of the opsin onto an image of the retina.

22. The system of claim 17, wherein the instructions further cause the system to map the first opsin density onto an image of the retina.

23. The system of claim 17, wherein the instructions are configured to cause the one or more processors to determine the first opsin density from a plurality of equations having the general form:

$$\begin{cases} I_{Out}(x, y, \lambda_1, t) = P_{In}(\lambda_1)c(x, y, t)10^{-\left[\frac{D_R(x,y,\lambda_1,t)+D_M(x,y,\lambda_1,t)+}{D_0(x,y,\lambda_1)}\right]} \\ I_{Out}(x, y, \lambda_2, t) = P_{In}(\lambda_2)c(x, y, t)10^{-\left[\frac{D_R(x,y,\lambda_2,t)+D_M(x,y,\lambda_2,t)+}{D_0(x,y,\lambda_2)}\right]} \\ \vdots \\ I_{Out}(x, y, \lambda_n, t) = P_{In}(\lambda_n)c(x, y, t)10^{-\left[\frac{D_R(x,y,\lambda_n,t)+D_M(x,y,\lambda_n,t)+}{D_0(x,y,\lambda_n)}\right]} \end{cases}$$

where (x,y) is a spatial point, c(x,y,t) is a lump optics factor, t is a time point, where $\lambda_1$ is the first wavelength, $I_{Out}(x,y,\lambda_1,t)$ is the intensity of the reflected light at the spatial point, the first wavelength and the time point, $P_{In}(\lambda_1)$ is the power of the illuminating light signal at wavelength $\lambda_1$, $D_R(x,y,\lambda,t)$ is the double-pass optical density of rhodopsin at the first wavelength, the spatial point and the time point, $D_M(x,y,\lambda,t)$ is the double-pass optical density of metarhodopsin III at the spatial point, the first wavelength and the time point, and $D_0(x,y,\lambda)$ is the double-pass optical density of a photo-stable pigment at the spatial point and the first wavelength, where $\lambda_2$ is the second wavelength, $I_{Out}(x,y,\lambda_2,t)$ is the intensity of the reflected light at the spatial point, the second wavelength and the time point, $P_{In}(\lambda_2)$ is the power of the illuminating light signal at wavelength $\lambda_2$, $D_R(x,y,\lambda_2,t)$ is the double-pass optical density of rhodopsin at the second wavelength, the spatial point and the time point, $D_M(x,y,\lambda_2,t)$ is the double-pass optical density of metarhodopsin III at the spatial point, the second wavelength and the time point, and $D_0(x,y,\lambda_2)$ is the double-pass optical density of a photo-stable pigment at the spatial point and the second wavelength, and where $\lambda_n$ is the nth wavelength, $I_{out}(x,y,\lambda_n,t)$ is the intensity of the reflected light at the spatial point, the second wavelength and the time point $P_{In}(\lambda_n)$ is the power of the illuminating light signal at wavelength $\lambda_n$, $D_R(x,y,\lambda_n,t)$ is the double-pass optical density of rhodopsin at the nth wavelength, the spatial point and the time point, $D_M(x,y,\lambda_n,t)$ is the double-pass optical density of metarhodopsin III at the spatial point, the nth wavelength and the time point, and $D_0(x,y,\lambda_n)$ is the double-pass optical density of a photo-stable pigment at the spatial point and the nth wavelength.

24. The system of claim 17, wherein the instructions are configured to synchronize generation of the at least three illumination light signals, and a plurality of corresponding exposure times for the light detector.

25. The system of claim 17, further comprising a galvanometer configured to direct the at least three illumination signals to the retina according to a raster scanning scheme.

26. The system of claim 17, further comprising an annulus mirror configured to direct the at least three illumination light signals from the one or more light sources to the retina, the annulus mirror including an aperture configured to allow the reflected light signals to pass from the retina to the light detector.

\* \* \* \* \*